United States Patent
Zehler et al.

(10) Patent No.: US 9,933,359 B2
(45) Date of Patent: Apr. 3, 2018

(54) VENDOR EXCLUSIVITY SECURITY FEATURE FOR PAPER-BASED DIAGNOSTIC SOLUTION

(71) Applicant: Xerox Corporation, Norwalk, CT (US)

(72) Inventors: Peter J. Zehler, Penfield, NY (US); Jing Zhou, Webster, NY (US); Nancy Y. Jia, Webster, NY (US)

(73) Assignee: XEROX CORPORATION, Norwalk, CT (US)

( * ) Notice: Subject to any disclaimer, the term of this patent is extended or adjusted under 35 U.S.C. 154(b) by 292 days.

(21) Appl. No.: 14/806,412

(22) Filed: Jul. 22, 2015

(65) Prior Publication Data

US 2017/0023465 A1    Jan. 26, 2017

(51) Int. Cl.
  *G01N 21/25* (2006.01)
  *G01N 21/84* (2006.01)
  *G01N 21/78* (2006.01)

(52) U.S. Cl.
  CPC ......... *G01N 21/253* (2013.01); *G01N 21/251* (2013.01); *G01N 21/8483* (2013.01); *G01N 21/78* (2013.01)

(58) Field of Classification Search
  CPC .. G01N 21/253; G01N 21/8483; G01N 21/78; G01N 21/251
  See application file for complete search history.

(56) References Cited

U.S. PATENT DOCUMENTS

| | | | | |
|---|---|---|---|---|
| 5,279,790 A * | 1/1994 | Corey | ................ | C07D 209/12 422/420 |
| 6,770,487 B2 * | 8/2004 | Crosby | ................ | G01N 33/558 422/547 |
| 7,344,081 B2 * | 3/2008 | Tseng | ................ | G01N 21/8483 235/375 |
| 7,454,880 B1 | 11/2008 | Austin et al. | | |
| 7,723,120 B2 * | 5/2010 | Xiao | ................ | B01L 3/50273 137/375 |
| 7,768,645 B2 * | 8/2010 | Roman | ............. | G01N 21/8483 356/406 |
| 7,885,444 B2 * | 2/2011 | Wang | ................ | G01N 21/8483 382/128 |
| 7,969,624 B2 | 6/2011 | Mestha et al. | | |
| 8,105,552 B2 * | 1/2012 | Xiao | ................ | B01L 3/50273 422/502 |
| 8,249,879 B2 | 8/2012 | Bangalore et al. | | |
| 8,377,710 B2 | 2/2013 | Whitesides et al. | | |
| 8,628,729 B2 | 1/2014 | Carrilho et al. | | |
| 8,730,460 B2 | 5/2014 | Yan et al. | | |

(Continued)

*Primary Examiner* — Manav Seth
(74) *Attorney, Agent, or Firm* — Fay Sharpe LLP

(57) ABSTRACT

Disclosed herein is a paper based diagnostic device including a portable biomedical diagnostic device comprising, paper, wax, and reagents. The biomedical diagnostic device can analyze biochemical assays in test fluids such as blood, urine, and saliva. Diagnostic devices can include one or more of tracking information, personal identification information, security information, color calibration information, and environmental indicators. The security information can further include keys or codes identifying one or more unique characteristics. One aspect of the security information ensures that only predeterminable vendors are able to determine the results of a test from the diagnostic devices.

15 Claims, 6 Drawing Sheets

(56) References Cited

U.S. PATENT DOCUMENTS

| | | | |
|---|---|---|---|
| 8,815,532 B2* | 8/2014 | Kovalenko | C12Q 1/28 435/28 |
| 8,821,810 B2* | 9/2014 | Whitesides | B01L 3/502738 422/420 |
| 8,969,085 B2* | 3/2015 | Sharpe | G01N 33/02 422/400 |
| 9,131,893 B2* | 9/2015 | Faybishenko | A61B 5/14507 |
| 9,285,323 B2* | 3/2016 | Burg | G01N 21/78 |
| 9,346,048 B2* | 5/2016 | Zhou | B01L 3/5023 |
| 9,365,019 B2* | 6/2016 | Zhou | B32B 37/0046 |
| 9,445,749 B2* | 9/2016 | Erickson | G01N 33/52 |
| 9,506,855 B2* | 11/2016 | Papautsky | G01N 21/25 |
| 9,557,274 B2* | 1/2017 | Barstis | G01N 33/552 |
| 9,586,204 B2* | 3/2017 | Hong | B01L 3/5023 |
| 9,686,540 B2* | 6/2017 | Zhou | H04N 17/02 |
| 2007/0061393 A1 | 3/2007 | Moore | |
| 2011/0111517 A1* | 5/2011 | Siegel | B01L 3/502707 436/164 |
| 2011/0123398 A1 | 5/2011 | Carrilho et al. | |
| 2011/0189786 A1* | 8/2011 | Reches | B01L 3/5088 436/164 |
| 2012/0053930 A1 | 3/2012 | Bangalore et al. | |
| 2012/0178176 A1* | 7/2012 | Haas | G01N 21/293 436/164 |
| 2012/0181184 A1 | 7/2012 | Whitesides et al. | |
| 2012/0198685 A1 | 8/2012 | Bernardina Junior | |
| 2012/0257188 A1* | 10/2012 | Yan | G01N 33/49 356/40 |
| 2013/0034869 A1* | 2/2013 | Whitesides | B01L 3/502738 435/7.92 |
| 2013/0034908 A1* | 2/2013 | Barstis | G01N 31/22 436/43 |
| 2013/0084630 A1* | 4/2013 | Rolland | G01N 21/78 435/287.8 |
| 2014/0001058 A1* | 1/2014 | Ghaffari | G01N 27/327 205/792 |
| 2015/0116093 A1* | 4/2015 | Swager | G06K 19/0717 340/10.4 |
| 2016/0080548 A1* | 3/2016 | Erickson | H04M 1/72527 455/556.1 |

\* cited by examiner

VENDOR EXCLUSIVITY SECURITY FEATURE FOR PAPER-BASED DIAGNOSTIC SOLUTION

INCORPORATION BY REFERENCE

U.S. Pat. No. 7,969,624, issued Jun. 28, 2011, by Mestha et al. and entitled "METHOD AND SYSTEM FOR IDENTIFYING OPTIMAL MEDIA FOR CALIBRATION AND CONTROL";

U.S. Pat. No. 7,454,880, issued Nov. 25, 2008, by Austin et al. and entitled "PERSONALIZED MEDICATION PACKAGING"; and U.S. Publication No. 2007/0061393, published Mar. 15, 2007, by James E. Moore and entitled "MANAGEMENT OF HEALTH CARE DATA", are incorporated herein by reference in their entirety.

CROSS REFERENCE TO RELATED PATENT AND APPLICATIONS

U.S. patent application Ser. No. 14/799,832, filed Jul. 15, 2015, by Hong et al. and entitled "DESIGN OF PAPER SENSOR";

U.S. patent application Ser. No. 14/799,969, filed Jul. 15, 2015, by Zhou et al., and entitled "ROBUST COLORIMETRIC PROCESSING METHOD FOR PAPER BASED SENSORS";

U.S. Provisional Patent Application No. 62/041,191, filed Aug. 25, 2014, by Jia et al., and entitled "PAPER SENSING AND ANALYTIC SERVICE WORKFLOW METHODS AND SYSTEMS", U.S. patent application Ser. No. 14/312,061, filed Jun. 23, 2014, by Zhou et al., and entitled "APPARATUS FOR FORMING HYDROPHOBIC STRUCTURES IN POROUS SUBSTRATES";

U.S. patent application Ser. No. 14/312,209, filed Jun. 23, 2014, by Zhou et al., and entitled "APPARATUS FOR PRODUCING PAPER-BASED CHEMICAL ASSAY DEVICES";

U.S. patent application Ser. No. 14/311,970, filed Jun. 23, 2014, by Beachner et al., and entitled "SYSTEM AND METHOD FOR FORMING BONDED SUBSTRATES";

U.S. patent application Ser. No. 14/311,909, filed Jun. 23, 2014, by O'Neil et al., and entitled "SYSTEM AND METHOD FOR FORMING HYDROPHOBIC STRUCTURES IN A POROUS SUBSTRATE"; are incorporated herein by reference in their entirety.

BACKGROUND

Paper-based sensing includes a paper-based diagnostic device comprising a portable biomedical device made of paper, wax, and reagents that can analyze biochemical assays in test fluids such as blood, urine and saliva. The devices are small, lightweight and low-cost and have potential applications as diagnostic devices in healthcare, military and homeland security, to mention a few. One aspect of a security measure is to ensure that only the vendor that issued the device, and/or designated entities, are able to determine or "read" the results of the test from said device.

BRIEF DESCRIPTION

In one embodiment of this disclosure, described is a paper based sensor method comprising: applying a test sample of a substance to a paper-based sensor, the paper-based sensor reacting to the test sample to generate one or more color indicators; capturing an image of the paper-based sensor after the test sample is applied to the paper-based sensor; performing colorimetric image processing of the captured image of the paper-based sensor to determine one or more colorimetric properties associated with the paper-based sensor, the colorimetric properties indicating one or more attributes associated with the test sample; wherein the paper-based sensor includes one or more of tracking information, personal identification information, security information, color calibration information, and environmental indicators; and, wherein the security information includes a key to decode at least one unique characteristic.

In another embodiment of this disclosure, described is a paper-based sensor processing system comprising: a processor and associated memory configured to receive a captured image of a paper-based sensor after a test sample is applied to the paper-based sensor, the processor and associated memory configured to execute instructions to perform a method comprising: performing colorimetric image processing of the captured image of the paper-based sensor to determine one or more colorimetric properties associated with the paper-based sensor, the colorimetric properties indicating one or more attributes associated with the test sample; wherein the paper-based sensor includes one or more of tracking information, personal identification information, security information, color calibration information, and environmental indicators; and, wherein the security information includes a key to decode at least one unique characteristic.

In still another embodiment of this disclosure, described is a computer program product comprising: a non-transitory computer-usable data carrier storing instructions that, when executed by a computer, cause the computer to perform a method comprising: performing colorimetric image processing of a captured image of a paper-based sensor after a test sample is applied to the paper-based sensor, the colorimetric image processing determining one or more colorimetric properties associated with the paper-based sensor and the colorimetric properties indicating one or more attributes associated with the test sample; wherein the paper-based sensor includes one or more of tracking information, personal identification information, security information, color calibration information, and environmental indicators; and, wherein said security information includes a key to decode at least one unique characteristic.

DETAILED DESCRIPTION

As discussed in the background, paper-based sensors (i.e. paper-based test devices) are an emerging technology that have advantages relative to traditional test strips in terms of cost and multiplexing. The concern of poor accuracy associated with a paper-based sensor and paper test strip, due to colorimetric measurements, has limited them from quantitative applications. For an existing test strip application, a user has to manually compare resultant color to a set of color reference cards. This is neither user friendly nor reliable. Recently some companies have attempted to develop phone 'apps' to automate the test strip reading process using a phone camera.

The present disclosure provides a novel end-to-end workflow/solution to enable real-time patient or user health condition monitoring and feedback. User monitoring comprises health condition monitoring, including homecare, self-administered monitoring, health/wellness screening, risk assessment, etc. The disclosed work flow/system solution includes printing of customized security and sensing information, printing of bio-reagents applications, a colorimetric process method, and a software platform. This end-to-end workflow provides robust and accurate result reading and patient feedback using paper-based sensors with various different cameras and various different lighting conditions. Unlike a test strip application where a color reference card is required, the disclosed method and system prints a reference color along with a hydrophobic channel on a paper sensor substrate during a device fabrication process and provides the user with real-time quantitative results.

Figure 1:
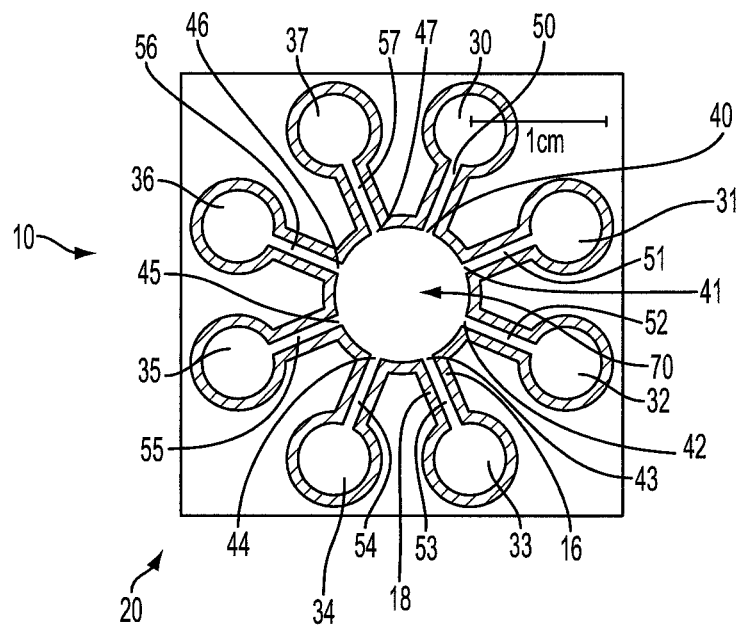
FIG. 1 represents one type of a paper-based sensor or test device.
Figure 2:
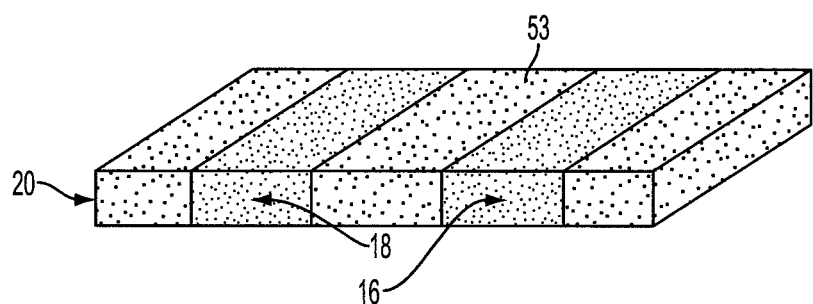
FIG. 2 represents an enlarged partial section of the paper-based sensor of FIG. 1.

A paper-based sensor or paper-based test device 10, as shown in FIGS. 1 and 2, is a small biomedical device made of paper, wax, and reagents that can analyze bioassays in test fluids or test liquids such as blood, urine and saliva. The hydrophobic barrier walls 16, 18 are made of wax that can penetrate through the entire thickness of the paper 20 (i.e. hydrophilic matrix) to create and separate (i.e. divide) various fluidic components such as a series of test regions 30, 31, 32, 33, 34, 35, 36, 37, fluid entrances 40, 41, 42, 43, 44, 45, 46, 47, transport channels 50, 51, 52, 53, 54, 55, 56, 57, and mixers or reagents. The transport channels 50-57, can be hydrophobic (i.e. wax) channels extending through the hydrophilic matrix paper 20. Various reagents with various and/or different concentrations can be pre-deposited on the test regions 30-37. During the diagnostic process, capillary forces pull portions of the test fluid 70 to associated multiple test regions 30-37 and upon contacting the pre-deposited reagents, react with the respective portions of test fluid 70. A signal, color change, or color shade is generated if a specific analyte is present in the test fluid 70; for instance, a color shade or change develops where the color density varies as a result of the concentration of the analyte. The color change or shade can be captured and recorded by an imaging device such as a smart phone or camera phone and can then be processed by an algorithm to calculate the concentration of each analyte based on a calibration curve or color scale of the device. The diagnostic results and/or raw data (if the image processing and diagnostic analysis is done on the server side) can be uploaded to a data server where the user's or patient's history can be stored for inquiry and advanced data analytics can be performed which can help to detect and prevent adverse health conditions/diseases. It is to be appreciated that the user's data analytics can be used for trend monitoring, health screening, risk assessment, et al.; the results of which can include non-adverse health conditions.

Paper based sensors have several advantages over traditional test strips. Test strips are simplex (one test per test strip), while paper sensors can be multiplex (multiple tests on one test device). Traditional test strips require relatively more test fluid than paper sensors. Test strips are fabricated by analog technology, while paper sensors can be digitally printed and quantitatively analyzed which enables greater customization and personalization.

Traditional test strips require users to manually measure a color with a color reference card, which can be unreliable and limits their application in quantitative measurement. Software has been developed to automate the test strip measurement process with a phone camera. However, a color reference card is typically used to calibrate a camera RGB (Red-Green-Blue) space and the total intensity is used for concentration measurement.

Use of paper based sensors is an emerging technology that provides advantages over traditional test strips in terms of reducing costs and multiplexing. Current paper based sensors require a user to provide a certain amount of test liquid (blood, urine, etc.) to ensure the accuracy of the test. The level of multiplexing is typically limited by the printing resolution and straightness of printed wax vertical walls/barriers. Additionally, the current method of reading colorimetric information typically uses either a separate manual reference card or uses a mobile application available in the market that can suffer from the variability of individual reading devices (camera, illumination, light conditions, surrounding light conditions, etc.). Thus, it is important to develop novel designs for paper based sensors that can achieve a higher level of multiplexing than the current devices available in the market, and can provide higher readout accuracy and proprietary processing regardless of the variation from individual reading devices.

The present disclosure provides an overall workflow associated with a paper sensor device, and method of use thereof, including the printing of customized security information and device condition indicators, printing of bio-reagents, a colorimetric process method, a software platform, and assignment of unique identifiers.

In another exemplary embodiment (FIG. 3), a paper sensor device 200 can include the following components: a structural forming layer 216, an optional filter membrane layer 212, and at least two laminating layers 218, 220. The structure forming layer 216 can include a channel structural area 224, a test area 210, a calibration reference area 226, and an auxiliary information area 228.

The test area or test zone 210 can include 1 to n (n>=2) individual segmented test zones 230, 231, 232, 233, 234, 235. The segmented test zones 230-235 can be arranged in an axially symmetric or axially radiating manner. The total test area 210 is from about 25% to about 60%, and preferably at least 37.5% of the total device area 202. The area of individual test zones 230-235 can be at least about 5 mm². Comparing to the prior art devices (FIG. 1), the individual test zones 230-235, of the present disclosure, are at least three (3) times larger. Test zones 230-235 are surrounded and divided by wax ink barrier walls 236, 237, 238, 239, 240, 241 (i.e. solid ink barriers) with a minimal wall width of about 100 um for maximizing the area of the test regions or zones 230-235 relative to a limited space or area for the device 202. It is to be appreciated that a majority of the volume of a test sample is utilized and reaches, i.e. reacts with, the reagents in each of the test zones 230-235.

One exemplary test panel can include respective reagents in test zones 230-235 for measuring levels of triglyceride, total cholesterol, HDL (i.e. three individual test zones). Another exemplary test panel can include respective reagents in test zones for measuring lipid panel, i.e. levels of triglyceride, total cholesterol, HDL, Hemoglobin A1C (HbA1C), glucose (i.e. five individual test zones). In the aforementioned manner, each test zone 230-235 has a different reagent. It is to be appreciated that each test zone can alternatively have a different concentration of the same reagent to measure different levels of a single bioassay.

Auxiliary information or identifying text (for example, GL, TG, HbA1C, HDL, TC labels; manufacturer name and date; etc.) that indicates the type of test in each test zone 230-235 can be printed outside and adjacent to the test zones or regions (i.e. auxiliary information 228). Auxiliary information or identifying text (for example, GL represents glucose, TG represents triglyceride, A1C represents hemoglobin, HDL represents HDL cholesterol, and TC represents total cholesterol) labels the type of test in each test zone 230-235 and can be printed outside and adjacent to the test zones or regions (i.e. reference regions).

The optional filter membrane layer 212 can have a separation membrane 217 (i.e. plasma separation) that covers the total test area 210. Alternatively, the optional filter membrane 217 can have a partial separation membrane and partial "other materials" (i.e. paper) to enable controlled flow of the test sample. The plasma separation membrane 217 can include a series of pores on the top surface as well as the bottom surface. The series of pores can have a pore sized gradient between the top surface and the bottom surface. In particular, the pore size on the top surface can be greater than the pore size on the bottom surface.

Figure 3:
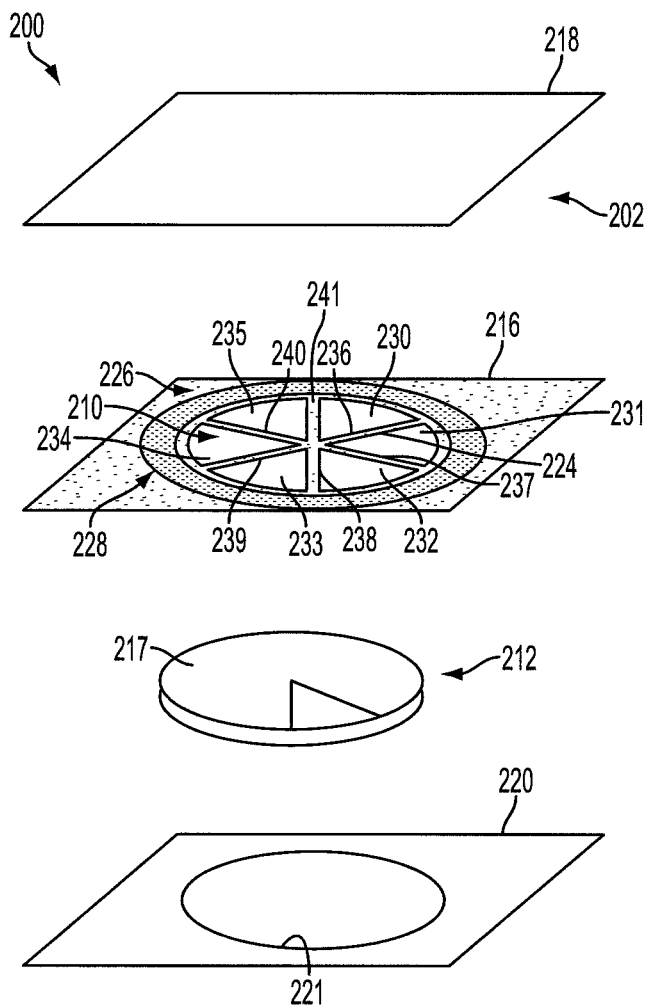
FIG. 3 is an exploded view of a paper-based sensor according to the present disclosure.

Membrane layer 212 and structural forming layer 216 can be sandwiched between laminate film layers 218, 220. A hole 221 that is smaller than the size of the membrane 217 can be cut in the bottom lamination layer 220 at the backside of the device (FIG. 3). The plasma separation membrane 217 is visible on the backside of the device 200 when the device 200 is in the assembled arrangement.

Referring again to FIG. 3, the present disclosure proposes a design of a biomedical paper sensor 200 which can determine the concentration of biological materials in test fluids such as blood, urine, and saliva. The sensor 200 can contain axially radiating and/or axially symmetric test zones 230-235 arranged similar to slices of a pie (for example) divided by wax ink barriers 236-241 formed by a process that produces thin walls. Each test zone 230-235 can contain a unique test reagent and can be identified by printed text (not shown) in area 228. The region 226 of the device outside of the test zone 230-235 can be printed with a uniform reference color. Additionally, the color of the wax wall can also serve as a reference color when it is not clear. Benefits of the sensor 200 include increased accuracy in the measurement of the concentration of biological materials due to the larger area of the test zones. Benefits also include the integration of the reference or calibration color 226 into the sensor 200 which simplifies a visual calibration review, check, or comparison for quantification of the concentration of the test fluid (i.e. test sample).

Figure 4:
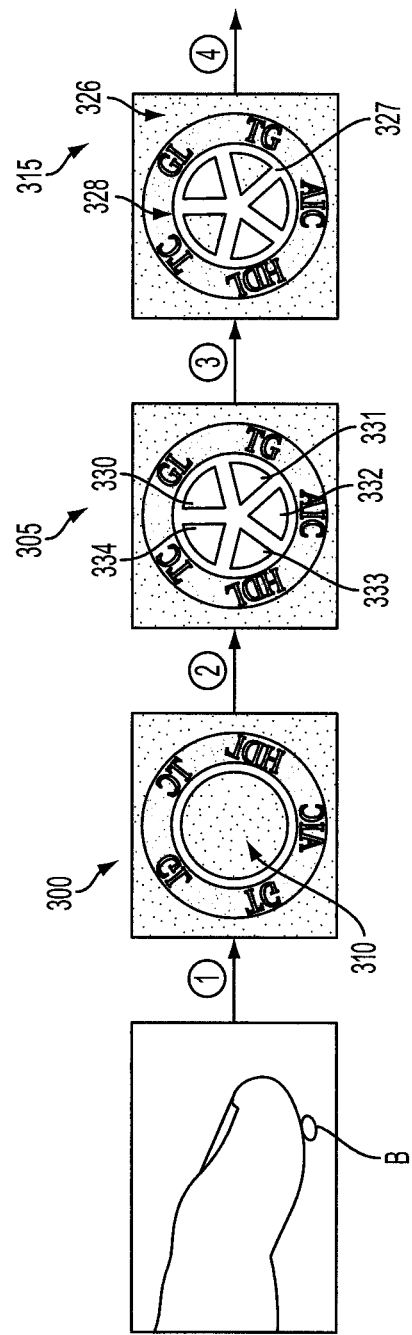
FIG. 4 shows the processing of a blood sample by an exemplary paper sensor device according to an exemplary embodiment of this disclosure.

FIG. 4 illustrates the processing of a blood sample by an exemplary paper sensor device 300 according to an exemplary embodiment of this disclosure. FIG. 4 displays a method of using the paper sensor device 300. A blood sample B is taken from a patient or user and placed or "sucked" into the bottom of the device, i.e. the test area 310, of the paper sensor 300 (step 1). The paper sensor 300 can be turned right side up wherein the blood sample processing can be viewed (step 2). The assay development 305 proceeds in which the blood sample B makes contact with the respective reagents in the test zones 330, 331, 332, 333, 334 (step 3). After the sample has reacted to the reagents, the developed assay 315 is subsequently formed (step 4).

Referring again to FIG. 4, wherein an exemplary triglyceride paper sensor 300 is therein displayed. Identifying a reference or calibration color area can include substrate regions 327, 328 between the test zones 330, 331, 332, 333, 334, and a calibration color area or region 326. Areas 326, 327, and 328 can be used as reference color areas or contrast color areas. Areas 327 and 328 can be any color to provide contrast (black, color, contrast color, etc.) between the test zones 330-334 and reference areas 326, 327, and 328. It is to be appreciated that the calibration reference area 326 can be separated into multiple sub-areas including separate reference colors associated with each sub-area (not shown). The multiple color reference areas enable use of reagents with different dye colors in test zones 330-334. Alternatively, the reference region can include a first calibration color area including a first predeterminable color for comparing to one or more of the axial test zones. The reference region can further include a second calibration color area including a second predeterminable color for comparing to one or more of the axial test zones. The first and second calibration color areas can each include first and second predeterminable colors, respectively, for comparing to one or more of the axial test zones to report or indicate the concentration of at least two test substance analytes based on the calibrated reading in each test area. In one embodiment, the substrate region 328 can include a contrasting color to distinguish between the test zones 330-334 and the calibration color area 326. Although not shown in FIG. 4, the triglyceride paper sensor 300 can display a gradient of color change in the test zones 330-334 due to different concentrations of the triglyceride. The color change or color shade of test zones 330-334 can be compared to the reference color 326 (i.e. magenta). It is to be appreciated that the color change or color density represents the concentration of triglyceride (for example) from associated test zones 330, 331, 332, 333, 334, and can include varying concentrations (mg/dL). In this manner, the biomedical paper sensor 300 is used for determining a concentration of biological materials contained in fluids (i.e. blood sample). It is to be appreciated that the paper sensor device 300 performs sample collection; sample processing and assay development 305; and, assay readout 315. The sensor 300 also incorporates a calibration reference area 326, and reference or substrate areas 327, 238.

Identifying a reference or calibration color area can include substrate regions 327 and 328 between the test zones 330-334 and a calibration color area or region 326. The substrate regions 327 and 328 can include contrasting colors to distinguish between the test zones and the calibration color area 326. In the example shown in FIG. 4, the paper sensor 300 can display a gradient of color change in the test zones 330-334 due to different types of reagents, and/or different concentrations of a reagent, that can measure different levels of a bioassay. It is to be appreciated that each type of analyte (GL, TG, HbA1C, HDL, TC) can use a different reagent, and each analyte/reagent pair can have an associated calibration curve for color reference. Additionally, for a single analyte assay determination, color change in the test zones 330-334 can be due to different concentrations of the same reagent in each test zone.

Figure 5:
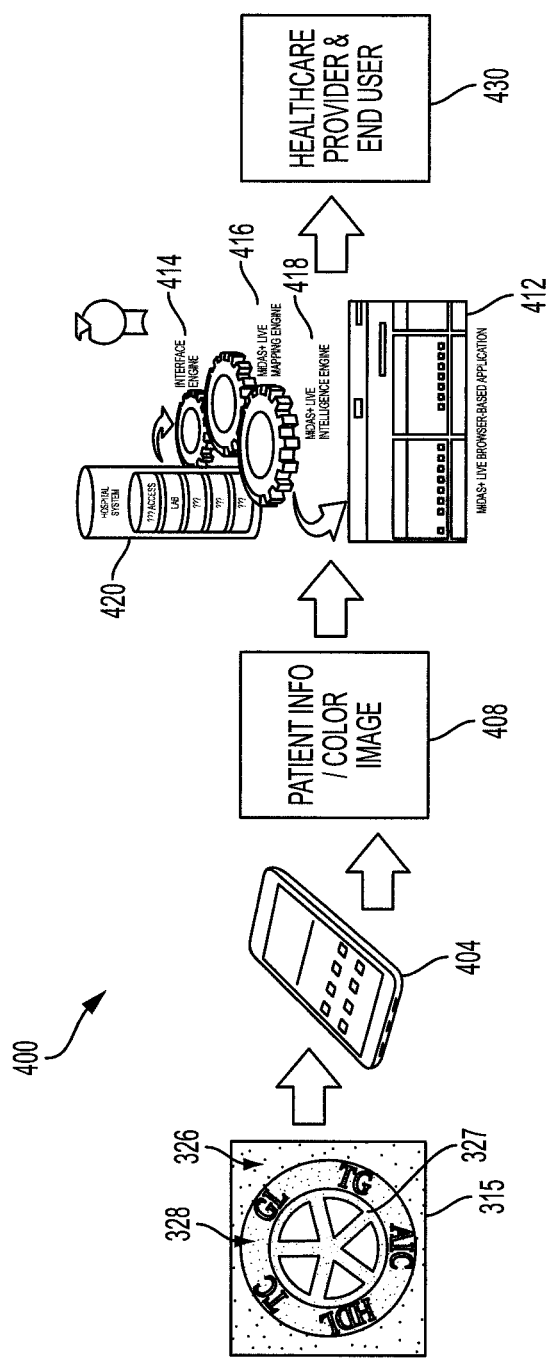
FIG. 5 is an exemplary embodiment of a Paper Sensing and Analytic Service (PSAS) workflow according to an exemplary embodiment of this disclosure.
Figure 6:
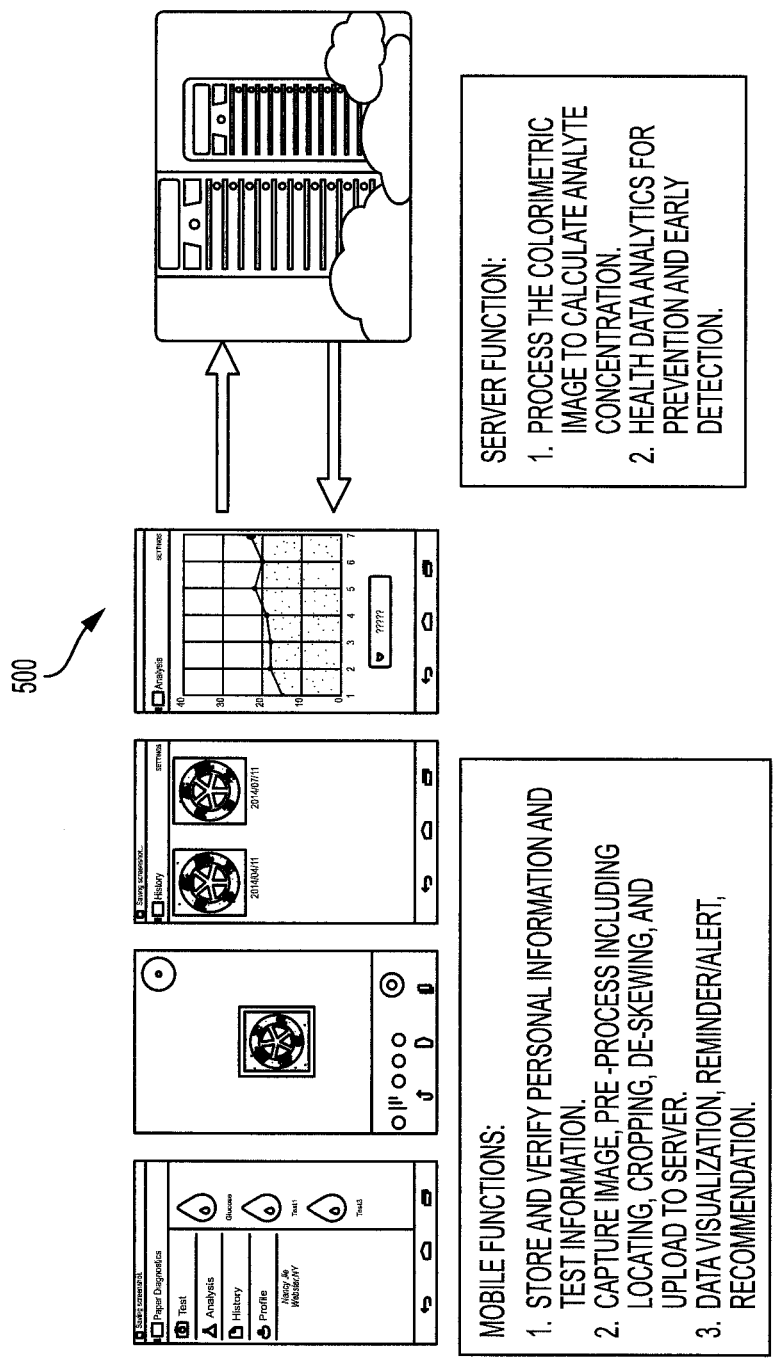
FIG. 6 is an exemplary platform for implementing a paper device sensor workflow according to this disclosure; and, FIG. 7 shows an exemplary paper sensing device fabrication process according to this disclosure.

FIGS. 5 and 6 illustrate an exemplary embodiment of a Paper Sensing and Analytic Service (PSAS) workflow according to the present disclosure. FIG. 5 demonstrates the PSAS workflow 400 that begins with the biomedical paper sensor 300 including a fluid sample collected, processed, developed, and the resulting assay 315 displayed. The assay development and display 315 can be photographed and uploaded to, for example, a cell phone 404. Once uploaded, the resultant assay 315 can be transmitted 408 to a browser based application 412 that includes an interface engine 414, mapping engine 416, and intelligence engine 418. The browser based application 412 can reside in a healthcare system database 420 that connects patient information/access, lab results, radiology, clinical, prescription. The assay results in the system database 420 can then be accessed by a healthcare provider and/or end user 430 via an interfaced computer network and utilizing any various programs to ensure protected and secure access.

FIG. 6 illustrates an exemplary software platform 500 for implementing the paper device sensor workflow 400 according to this disclosure. As shown in FIG. 6, according to an exemplary embodiment, a smart phone including a camera and sufficient cpu computing power can perform all or partial image processing/analytics associated with the captured image in the local computers or through a server. For example, all image processing, etc. is performed utilizing a camera phone where diagnostic results are generated by the camera phone, i.e. smart phone, and uploaded to a server. Also, the server function can be cloud based according to an exemplary embodiment. The mobile functions include storing and verifying personal information and test information. Further, the mobile functions can capture the image, pre-process the image including locating, cropping, de-skewing, and uploading to the server. The functions further include data visualization, calibration, reminders/alerts, and/or recommendations. The server functions include processing the colorimetric image to calculate analyte concentrations. This workflow allows the end users and/or care providers, etc. to monitor health conditions instantly from their own home, care facilities, and elsewhere in a secure manner. As discussed, the health data analytics can be used for prevention and early detection of diseases and/or health problems.

Figure 7:
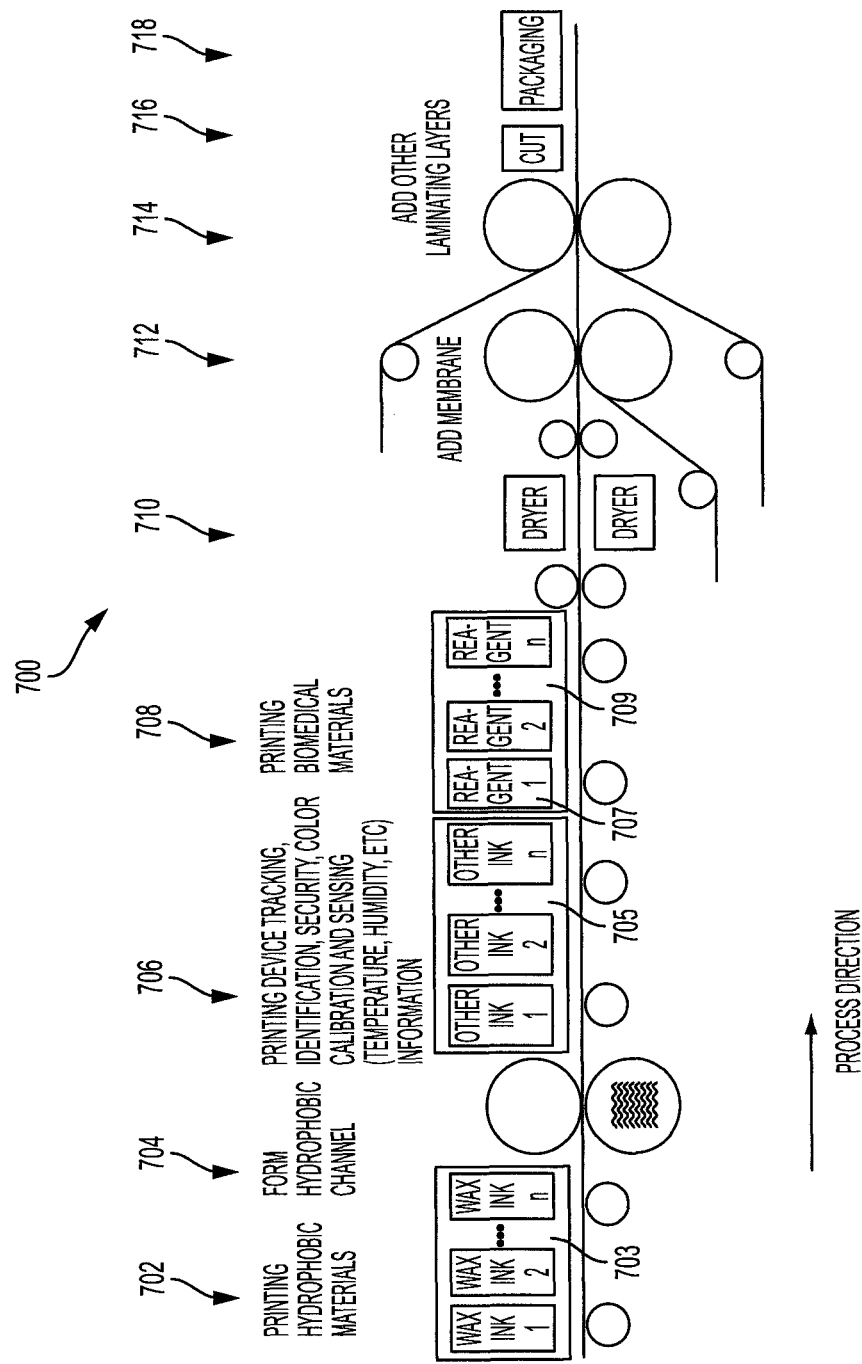

FIG. 7 illustrates a paper sensor device fabrication process/workflow 700. As shown in FIG. 7, the apparatus for fabricating the chemical assay devices includes a substrate transport configured to move a first hydrophilic substrate in a process direction, the process can include: a first print zone including at least one printhead to print solid/wax ink device structure (wells, channels etc.) 702; a structure formation unit to apply heat and pressure to enable wax ink to flow/penetrate through the paper substrate (forming hydrophobic channels) 704; print unique device tracking, identification, security and color calibration and device environmental health condition indicators (temperature, relative humidity, etc.) 706 (alternately this can be printed at 702); print biomedical materials and reagents 708; dry biomedical materials 710; cut filter membrane and add/align the material to the device structure 712; add other laminating layers and perform lamination 714; cut the devices to the desired shape and size 716; and package the product including assembled devices/testing strips, instructions, desiccant, etc. 718. The paper device (testing strip) environmental or health conditions, such as the expiration status of the reagents, can be monitored via the color change of a printed sensor in the device (for example, recording the history of temperature change or humidity change and send a warning signal if temperature or humidity exceed the normal ranges).

In addition, the information about the device manufacturer, manufacturing date, device category, device category, device function, device tracking number, and target population can be printed on the paper based diagnostic device and/or device packaging. The manufacturing information can be used to prevent counterfeits, protect the brand names, and provide traceability for accident investigations. The device information can be used to prevent fraud and errors where a diagnostic device associated with a first person does not become associated with a second person's identity. The manufacturing and device information together can be used to validate the device as all paper-based diagnostic devices have a limited shelf life.

Referring again to FIG. 7, the present disclosure proposes a set of security features for the portable biomedical device 200, 300 made of paper, wax, and reagents that can analyze biochemical assays in test fluids such as blood, urine, and saliva. The security features can establish customizable and proprietary elements on the device that can only be processed by selected entities. One security feature can include printing the device 200, 300 on media with distinctive and unique color characteristics 703. A second security feature is for the devices 200, 300 to contain multiple wells and can include reagents printed in different locations 705. A third security feature can vary the reagent 707 used to test for a particular biochemical. A fourth security feature can include doping the wells 709 with a dye or chemical that will slightly modify the resulting color of the test. Benefits of the present disclosure include providing techniques that prevent other companies from analyzing the results of test samples because the database that links the unique identifiers to the security features incorporated can be proprietary to the company deploying the device. The four security techniques described above provide for a large variation in the distinctive and unique response of any individual device.

The present disclosure proposes methods for restricting the accurate processing of the paper-based diagnostic device 200, 300 by adding unique identifiers and variations in color/orientation to the device 703, 705, 707, 709. In addition, using variable data printing each diagnostic device can be assigned a globally unique identifier. A color calibration field can also be printed to enable proper color determination for the media. The media used to print the device can now be varied and the color properties of the media can be associated with the distinctive and unique identifier of the device. The orientation of the reagents within the device can be randomized and associated with the unique identifier of the device. Once the device is used by the patient, the image of the device can be captured by the patient's mobile device and sent back to the appropriate vendor. The vendor can then match the device's unique characteristics and a proper analysis can be performed.

The present disclosure comprises a paper-based diagnostic device being produced by or distinguished for a particular vendor. The various fluidic components, such as, test region, fluid entrance, transport channel, and mixer can be printed. Using variable data printing a globally unique identifier can also be printed. The color of the media can be varied through the production run. Various reagents with different concentrations can be pre-deposited on the test regions. The location of these deposits can also be controlled via variable data printing. When appropriate, additional doping can be applied with the reagent to skew the results of the test. A color calibration field can also be added. The variable data which now includes the unique device identifier, media color, reagent orientation and the location and description of any additionally doped reagents is stored in a database. The database containing the above information is supplied with the devices to respective vendors. The information is input into the analysis software. It is to be appreciated that the analysis software can also be provided to healthcare providers. The vendor can then distribute the devices to the healthcare providers. The healthcare providers can then scan the devices provided to a patient. The healthcare providers can then associate the results for a specific device with the associated patient. The vendor that created the device and that will analyze the test results, along with the device itself, can shield any Protected Health Information. The patient can perform the appropriate test using the device and can use a mobile phone to capture an image of the devices test results. That image can contain the unique identifier, color calibration, and the sample/reagent results. The patient can then transmit the image back to the healthcare provider who will have the image analyzed by the analysis software to obtain the results. The results can then be sent to the patient and stored in the patient's medical record maintained by the healthcare provider.

Paper based diagnostic devices, including the production thereof of these devices, culminates in analyzing test results and handling the management of related health information. One of the issues is having an entity analyze and interpret results from a device, when said entity did not manufacture the device. Exemplary methods discussed above can provide each sensor with a global unique number or identifier. Identifiers can be associated with respective patients but it can also identify a specific device and can customize the placement of the re-agents in the various device areas so that the results can only be determined if one knows the location of the various re-agents in that device. One aspect of this customization is the ability to vary the device in such a way that only the originating device manufacturer is able to know where the re-agents are in order to analyze the color gradients to provide the results of the test. Other aspects include the ability to change the background color of the media (i.e. the color of the matrix paper 20) so that color will affect the image results when the re-agents react with the sample. The paper-based device can be modified so that just a straight forward reading of the colors isn't enough. The device has to be 'decoded' to understand the properties of the media, their color, and how they affect the results. The device can include a color code so that proprietary analysis software must be applied to adjust the color tests in the analysis software to obtain the results. Another aspect is the ability to add some doping to individual cells such that it will change the results, i.e. the color properties of the end result. By adding various dyes, one can slightly alter what the results of the test will look like. 'Reading' the specific device includes factoring out or decoding the color change or alteration from the doping chemical. In this manner, key coding can be established and the decoding system provides the proper key to be able to unlock and analyze the paper-based devices accurately.

Since each device can be uniquely identified, groups or sequences of devices can be assigned to a given healthcare provider or to a particular patient so that the system can track the usage of and sort the actual devices. Each paper-based device can have a unique ID and the system can record the unique IDs as they are being printed into packets of devices. The packets of devices can then be distributed to various healthcare providers, which will then in turn distribute a sub packet to the individual patient. The system can track not only what healthcare provider has received the devices, but also the healthcare provider can track what patient specific devices have been assigned to. It is to be appreciated that instead of just capturing the actual device and the results, one also captures the ID of the device as well as the color sample, and all of that data can be sent back to the test result collection software. The proprietary software can do some initial correlation of all of this information, send the results back to the service provider, and perform predictive analytics.

In one exemplary arrangement, the device vendor can hold the specific decoding information, in which case, the raw data would be eventually handed all the way back to the device vendor so that it could be properly interpreted and handed back to the service provider. In another exemplary arrangement, the device vendor can provide a decoding system to the service provider.

One of the benefits of paper-based sensor devices is low cost analysis of samples. Providing unique identifiers and decoding protocols enables the manufacturers of paper-based sensors to also be involved (i.e. employed) in the analysis and interpretation of test results.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use.

Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A paper-based sensor method comprising:
providing a paper sensor device including a test zone with multiple assay regions, each assay has a different concentration of a same reagent to measure different levels of a single test sample, the paper sensor device further including a calibration color area including a reference color;
after the single test sample has been applied to the paper-based sensor and reacted to the reagents, capturing an image of the paper-based sensor including one or more color indicators each associated with an assay region;
using a computer, performing colorimetric image processing of the captured image of the paper-based sensor to determine a concentration of analyte contained in the single test sample, the processing including comparing a color change of the assay regions to the reference color to determine the concentration of at least one analyte contained in the single test sample;
wherein the paper-based sensor includes one or more of tracking information, personal identification information, security information, color calibration information, and environmental indicators; and,
wherein said security information includes a key to decode at least one unique characteristic.

2. The paper-based sensor method according to claim 1, comprising:
communicating the concentration of the at least one analyte contained in the test sample to one or more of a patient and a caregiver.

3. The paper-based sensor method according to claim 1, comprising:
performing predictive analytics.

4. The paper-based sensor method according to claim 1, wherein the unique characteristic includes one or more of a unique identifier, color calibration field, orientation of the reagents, doping of reagents, and concentration of reagent.

5. The paper-based sensor method according to claim 1, wherein the paper-based sensor includes tracking information, environmental indicators and security information, and the method validates the captured image of the paper-based sensor based on one or more of the tracking information, environmental indicators and security information.

6. The paper-based sensor method according to claim 1, wherein capturing the image of the paper-based sensor comprises a camera phone.

7. A paper-based sensor processing system comprising:
a paper sensor device including a test zone with multiple assay regions, each assay has a different concentration of a same reagent to measure different levels of a single test sample, the paper sensor device further including a calibration color area including a reference color;
a processor and associated memory configured to receive a captured image of a the paper-based sensor after the single test sample has reacted to the reagents, the processor and associated memory configured to execute instructions to perform a method comprising:
performing colorimetric image processing of the captured image of the paper-based sensor to determine a concentration of analyte contained in the single test sample, the processing including comparing a color change of the assay regions to the reference color to determine the concentration of at least one analyte contained in the single test sample;
wherein the paper-based sensor includes one or more of tracking information, personal identification information, security information, color calibration information, and environmental indicators; and,
wherein said security information includes a key to decode at least one unique characteristic.

8. The paper-based sensor processing system according to claim 7, comprising:
communicating the one or more attributes associated with the test sample to one or more of a patient and a caregiver.

9. The paper-based sensor processing system according to claim 7, comprising:
performing predictive analytics.

10. The paper-based sensor method according to claim 7, wherein the unique characteristic includes one or more of a unique identifier, color calibration field, orientation of the reagents, doping of reagents, and concentration of reagent.

11. A computer program product comprising:
a non-transitory computer-usable data carrier storing instructions that, when executed by a computer, cause the computer to perform a method comprising:
after a single test sample has reacted to a reagent, receiving a captured image of a paper sensor device including a test zone with multiple assay regions, each assay has a different concentration of the reagent to measure different levels of the single test sample, the paper sensor device further including a calibration color area including a reference color;

performing colorimetric image processing on the captured image including comparing a color of the assay regions to the reference color to determine a concentration of at least one analyte contained in the single test sample, wherein the color of an assay region corresponds to the concentration of reagent in the assay region;

wherein the paper-based sensor includes one or more of tracking information, personal identification information, security information, color calibration information, and environmental indicators; and, wherein said security information includes a key to decode at least one unique characteristic.

12. The computer program product according to claim 11, the method further comprising:

communicating the concentration contained in the test sample to one or more of a patient and a caregiver.

13. The computer program product according to claim 12, the method further comprising:

performing predictive analytics.

14. The computer program product, according to claim 13, wherein the paper-based sensor includes tracking information, environmental indicators and security information, and the method validates the captured image of the paper-based sensor based on one or more of the tracking information, environmental indicators and security information.

15. The paper-based sensor method according to claim 14, wherein the unique characteristic includes one or more of a unique identifier, color calibration field, orientation of the reagents, doping of reagents, and concentration of reagent.

* * * * *